United States Patent
DeBuys et al.

(10) Patent No.: US 11,590,319 B2
(45) Date of Patent: Feb. 28, 2023

(54) MECHANICALLY-DECOUPLED ACTUATION FOR ROBOTIC CATHETER SYSTEM

(71) Applicant: Siemens Medical Solutions USA, Inc., Malvern, PA (US)

(72) Inventors: Christian DeBuys, College Station, TX (US); Young-Ho Kim, West Windsor, NJ (US); Ankur Kapoor, Plainsboro, NJ (US); Tommaso Mansi, Plainsboro, NJ (US)

(73) Assignee: Siemens Medical Solutions, Inc., Malvern, PA (US)

( * ) Notice: Subject to any disclaimer, the term of this patent is extended or adjusted under 35 U.S.C. 154(b) by 547 days.

(21) Appl. No.: 16/809,067

(22) Filed: Mar. 4, 2020

(65) Prior Publication Data

US 2021/0023337 A1    Jan. 28, 2021

Related U.S. Application Data

(60) Provisional application No. 62/877,622, filed on Jul. 23, 2019.

(51) Int. Cl.
*A61B 8/12* (2006.01)
*A61B 34/30* (2016.01)
(Continued)

(52) U.S. Cl.
CPC ............ *A61M 25/0113* (2013.01); *A61B 8/12* (2013.01); *A61B 8/445* (2013.01); *A61B 8/4466* (2013.01);
(Continued)

(58) Field of Classification Search
CPC ............ A61M 25/0113; A61M 25/105; A61M 25/0136; A61M 25/0133; A61M 25/01;
(Continued)

(56) References Cited

U.S. PATENT DOCUMENTS

| | | | |
|---|---|---|---|
| 2007/0185486 A1* | 8/2007 | Hauck | A61B 34/71 606/41 |
| 2008/0009791 A1* | 1/2008 | Cohen | A61M 25/0105 604/95.01 |

(Continued)

OTHER PUBLICATIONS

German Patent application No. DE 102019214868.9, filed on Sep. 27, 2019; Siemens Healthcare GmbH (The relevance of the foreign language reference is provided by the drawings.).

(Continued)

*Primary Examiner* — Tan-Uyen T Ho
*Assistant Examiner* — Regina Vahey

(57) ABSTRACT

For robotically operating a catheter, a medical catheter is controlled by rotation of the catheter as well as steering in one or more planes of a distal end of the catheter. To robotically rotate the catheter, a handle is rotated. The steering is performed separately using one or more knobs on the handle. The rotation of the handle complicates the robotic control of the knob. A mechanical decoupling is used so that rotation of the handle maintains the position of the knob relative to the handle. Gearing or transmission is used to avoid independent control of the knob and handle rotation. In an alternative or additional approach, the handle may be robotically controlled while also guiding the catheter shaft spaced away from the handle, allowing fine-tuned control of the catheter at the access point to the patient.

21 Claims, 3 Drawing Sheets

(51) Int. Cl.
*A61M 25/01* (2006.01)
*A61B 8/00* (2006.01)

(52) U.S. Cl.
CPC .... *A61M 25/0105* (2013.01); *A61M 25/0136* (2013.01); *A61B 2034/301* (2016.02)

(58) Field of Classification Search
CPC .......... A61B 2034/301; A61B 1/00042; A61B 2034/303; A61B 34/70; A61B 34/71; A61B 8/12; A61B 8/445; A61B 8/4466; A61B 1/00133; A61B 1/0016
See application file for complete search history.

(56) References Cited

U.S. PATENT DOCUMENTS

| | | | | |
|---|---|---|---|---|
| 2011/0028894 | A1* | 2/2011 | Foley | A61M 25/0136 604/95.01 |
| 2011/0065994 | A1* | 3/2011 | Kudoh | A61B 1/0016 600/146 |
| 2014/0277333 | A1* | 9/2014 | Lewis | A61M 25/0113 623/1.11 |
| 2016/0151115 | A1* | 6/2016 | Karguth | A61B 46/10 606/41 |
| 2020/0060646 | A1 | 2/2020 | Lindenroth et al. | |
| 2020/0061339 | A1 | 2/2020 | Lindenroth et al. | |

OTHER PUBLICATIONS

Stereotaxis, "Stereotaxs V-Drive Robotic Navigation System," Stereotaxis, [Online]. Available: http://www.stereotaxis.com/products/#l/vdrive. Accessed: Feb. 19, 2020.
U.S. Appl. No. 16/544,091, filed Aug. 19, 2019; Lindenroth, et al.; "Active Steering for Intracardiac Echocardiography Catheters".
U.S. Appl. No. 16/544,116, filed Aug. 19, 2019; Lindenroth, et al.; "Controlled Bending for Catheters".
Loschak, Paul M., et al. "A 4-DOF robot for positioning ultrasound imaging catheters." ASME 2015 International Design Engineering Technical Conferences and Computers and Information in Engineering Conference. American Society of Mechanical Engineers Digital Collection, 2015.

* cited by examiner

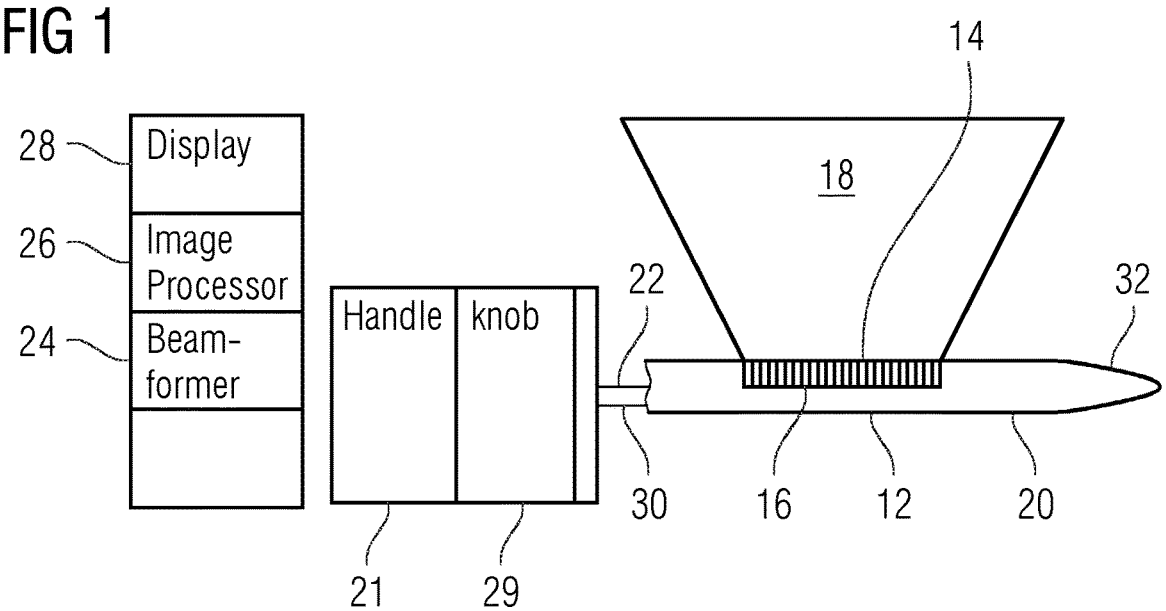
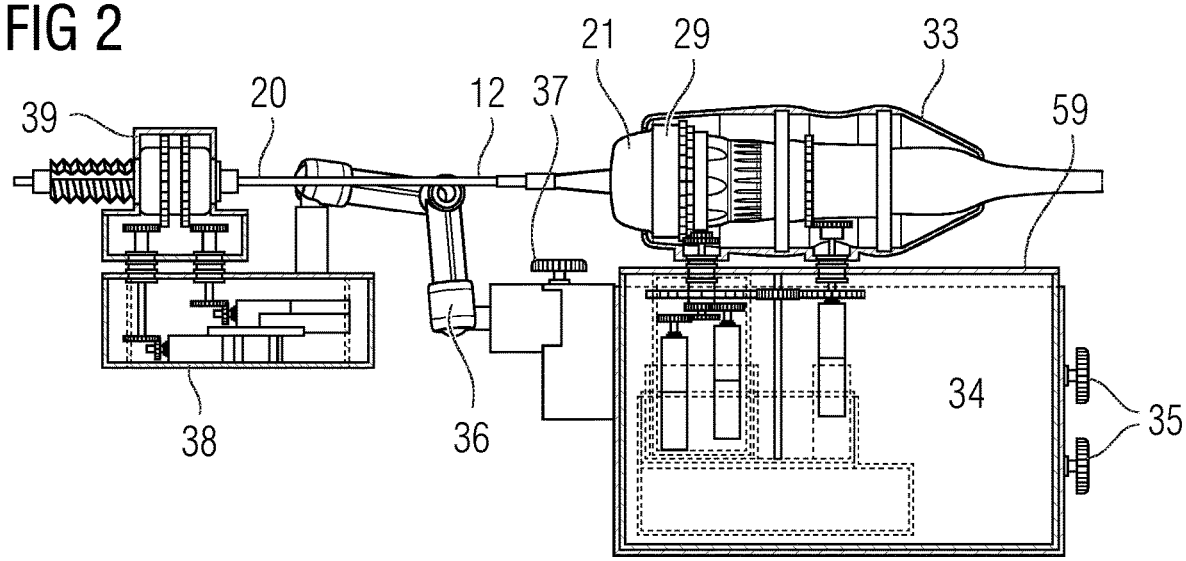

MECHANICALLY-DECOUPLED ACTUATION FOR ROBOTIC CATHETER SYSTEM

RELATED APPLICATION

The present patent document claims the benefit of the filing date under 35 U.S.C. § 119(e) of Provisional U.S. Patent Application Ser. No. 62/877,622, filed Jul. 23, 2019, which is hereby incorporated by reference.

BACKGROUND

The present embodiments relate to robotic control of a medical catheter. One example medical catheter is an intra-cardiac echocardiography (ICE) catheter, which is used for cardiac interventional and diagnostic procedures. ICE is able to provide close feedback of anatomical structures and tools during a surgical procedure.

One major challenge ICE and other interventional catheterization poses for the operating interventionalist is the difficult catheter manipulability. The ICE catheter is moved in a coordinated fashion with an interventional catheter. The operator manipulates multiple degrees of freedom simultaneously to achieve a desired pose as well as manages the coordination. A robotic system that controls the degrees of freedom (DOFs) of an ICE catheter may reduce the cognitive strain on the user.

One commercially-available robotic system for ultrasound catheter manipulation is the Stereotaxis Vdrive system. The mechanical design of this system controls only a limited number of degrees of freedom of the ICE catheter. For example, the precise control of the orientation of the catheter, which is necessary for appropriate imaging, may not be provided. Additionally, all motions are done at the handle, far from the insertion point, failing to account for the possibility of catheter buckling. Another proposed, automated system for a handheld ICE catheter has a large footprint and may be difficult to sterilize, making it unusable in a clinical setting

SUMMARY

By way of introduction, the preferred embodiments described below include methods, systems, and robots for robotically operating a catheter. A medical catheter is controlled by rotation of the catheter as well as steering in one or more planes of a distal end of the catheter. To robotically rotate the catheter, a handle is rotated. The steering is performed separately using one or more knobs on the handle. The rotation of the handle complicates the robotic control of the knob. A mechanical decoupling is used so that rotation of the handle maintains the position of the knob relative to the handle. Gearing or transmission is used to provide independent control of the knob and handle rotation. In an alternative or additional approach, the handle may be robotically controlled while also guiding the catheter shaft spaced away from the handle, allowing fine-tuned control of the catheter at the access point to the patient.

In a first aspect, a robotic catheter system includes a first motor configured by first gearing to rotate a catheter about a longitudinal axis. The robotic catheter system also includes a second motor configured by second gearing to rotate a first knob of a handle of the catheter. Third gearing connects between the first motor and the second motor so that the rotation of the catheter about the longitudinal axis by the first motor rotates the second motor to rotate the first knob.

In one embodiment, the first and second motors are servo motors. In another embodiment, a catheter handle housing and a base housing are provided. The first and second motors are in the base housing. The first and second gearing are in the catheter handle housing. The base housing is less than 16 inches long, 12 inches high, and 6 inches wide. As another embodiment, an arm connects with the base. The arm is jointed and connects to an access point housing configured to hold the catheter away from the handle at a point of entry into a patient. The base housing may have a second knob configured to adjust a position of the first and second motors relative to the base.

In another embodiment, the first knob comprises an anterior-posterior or a left-right knob for steering a distal end of the catheter. In a further embodiment, the first knob is rotatable relative to the handle and about the longitudinal axis. The third gearing is configured so that the first knob maintains a position relative to the handle while the handle rotates with the rotation of the catheter while the second motor is not activated.

In yet another embodiment, the first gearing includes a first gear matable with a second gear. The second gear extends around the handle so that rotation of the first gear by the first motor causes rotation of the second gear about the longitudinal axis.

For the third gearing, the third gearing including a gear with teeth around a cylindrical housing for the second motor according to one embodiment. Rotation of the first motor rotates the cylindrical housing and the second motor therein. In a further embodiment, the second motor is offset from a longitudinal center of the cylindrical housing. The second gearing includes a first shaft at the longitudinal center of the cylindrical housing so that the rotation of the cylindrical housing rotates the second motor about the longitudinal center.

For an embodiment with multiple knobs on the handle of the catheter, a third motor is within the cylindrical housing. Fourth gearing connects the third motor with a second knob of the handle. The fourth gearing includes a second shaft at the longitudinal center of the cylindrical housing. The first shaft is nested and rotatable independently of the second shaft.

In a second aspect, a method is provided for robotically operating a catheter. A first gear linked to the catheter is rotated so that the rotating of the first gear causes a handle of the catheter to rotate about a longitudinal axis of the handle. The rotation of the first gear is transmitted to a second gear so that rotation of the second gear causes rotation of a third gear linked to a knob of the handle.

In one embodiment, rotating the first gear includes rotating the first gear with a first motor. A second motor is configured to rotate the third gear. The transmitting includes transmitting where the rotation of the third gear is from rotation of the second gear and not powered by the second motor. In a further embodiment, the transmitting includes rotating a motor housing of the second motor where the second motor is mounted off-center in the motor housing. In another further embodiment, the third gear is rotated by the second motor independently of the rotating of the first gear. The rotating the third gear is not transmitted to the first gear.

In one example use, a base is positioned relative to a patient. The handle is positioned in a handle housing where the first gear is within the handle housing and connects with the base through a motor shaft. A position of the handle housing is adjusted relative to the base. The rotating then occurs after the adjusting.

In a third aspect, a system is provided for guiding a catheter. A handle housing is configured to hold a handle of the catheter. The handle housing has a first gear to rotate the handle and a second gear to rotate a first knob on the handle. A base is connectable with the handle housing so that the first and second gears are driven from the base. An access point housing is configured to hold a shaft of the catheter away from the handle. The access point housing is configured to adjust an angle of the shaft relative to the handle.

In one embodiment, a transmission in the base mechanically decouples actuation of the first gear from the second gear. The transmission includes a third gear on a first shaft with the first gear. The third gear links to a fourth gear on a housing of a first motor linked to a shaft with the second gear so that rotation of the first gear causes rotation of the third gear, which causes rotation of the housing so that the second gear rotates, allowing the first knob to maintain position relative to the handle. In a further embodiment, a fifth gear connects with and between the third gear and the fourth gear.

In yet another embodiment, an arm with one or more joints connects the base to the access point housing. The access point housing includes one or more motors for adjusting the angle.

The present invention is defined by the following claims, and nothing in this section should be taken as a limitation on those claims. Features of one aspect or type of claim (e.g., method or system) may be used in other aspects or types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a medical ultrasound system for imaging with an ICE catheter;

FIG. 2 illustrates one embodiment of a robotic system for guiding a catheter;

DETAILED DESCRIPTION OF THE DRAWINGS AND PRESENTLY PREFERRED EMBODIMENTS

Figure 3:
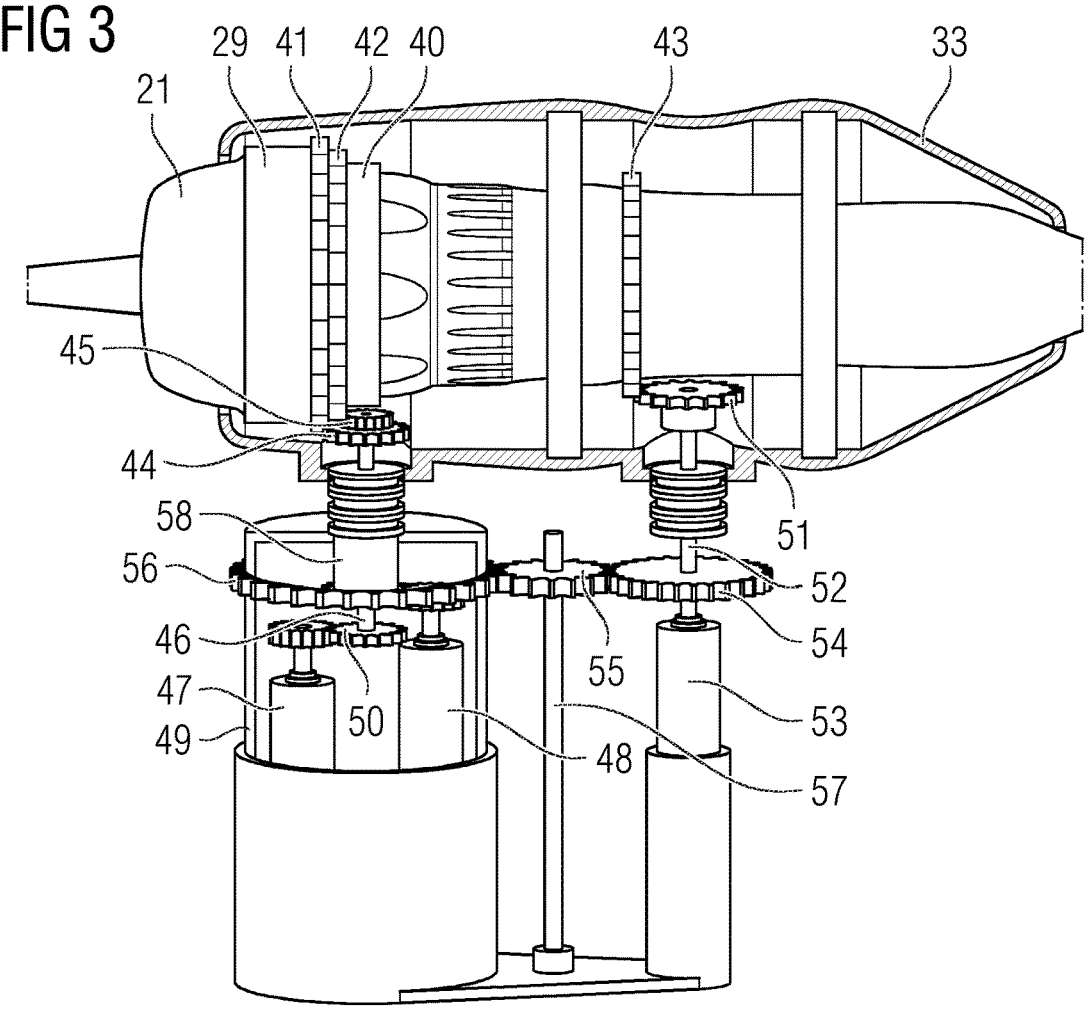
FIG. 3 illustrates gearing according to one embodiment for guiding a catheter.

A compact, sterilizable robotic catheter manipulator is provided for general-purpose access points. The manipulator includes mechanically decoupled actuation of handle rotation and knob-based manipulation. Commercially-available catheter systems are robotized in a clinical setting. In one embodiment, two sets of motion transmission setups are provided. The first, placed at the catheter handle, provides rotation of the handle, and control of the knobs that cause articulation of the flexible catheter body. The second is placed around the flexible catheter body itself and is placed near the insertion point in the patient. This second, optional, setup provides translation and rotation of the catheter while limiting buckling caused by friction from the insertion sheath. The end-effector of the medical device can be precisely positioned because the first setup can be used for larger vertical, yaw, and for-aft adjustments while an arm supporting the second setup may be moved for finer translational and angular adjustments.

Due to difficulties posed by control of a continuum manipulator such as an ICE catheter, the rotation of the catheter body is mechanically decoupled from the rotation of the knobs. The degrees of freedom for controlling the catheter are mechanically decoupled. Since the knob motions are mechanically decoupled from the whole-body rotation, the control effort is not burdened and can focus on more precise positioning of the catheter's sensor or of some other medical instrument.

The base of the device, which includes the motors, motor drivers, and adjustable degrees of freedom, is general purpose in that any device that can be fitted with an appropriate transmission system may be used with the base. The adjustable degrees of freedom and compactness of the base allow for surgeries at different access points (e.g., femoral, radial, or jugular) and precise alignment of the medical instrument, such as alignment of an ICE catheter with a sheath. The base is easily attached to the operating table or to another mobile table. The posability of the modular base allows for precise alignment of the catheter with the sheath. A plastic interface between the base and a transmission holding the catheter handle allows for the base to remain sterile so that the entire base is reusable and does not need to be cleaned.

The robotic system fits a standard, commercially-available ICE catheter, such as those in the Acunav family of catheters from Siemens. The sterile, modular robotic system provides for full-DOF robotic control of an ICE catheter. This system may be used for any kind of catheter or flexible medical instrument for insertion into a patient, including but not limited to bronchoscopes, flexible endoscopes, transthoracic echocardiography probes, trans-esophageal echocardiography probes, cardiac catheters for intervention (i.e., with medical tool for interaction with tissue of the patient), and any other type of catheter. This system may be used with a more-integrated system, in which the motion-driving elements and the imaging device are all integrated into one compact setup at production, as opposed to the embodiment described here, in which the imaging instrument and the robotic system are brought together at the time of use. Different methods for gripping and holding the catheter, for setting up the whole system, and/or for providing motion transmission may be used.

FIG. 1 shows an example medical ultrasound system for ICE. This example medical ultrasound system uses the ICE catheter 12, which may be robotically controlled. The medical ultrasound system includes the ICE catheter 12, a beamformer 24, an image processor 26, and a display 28. Additional, different, or fewer components may be provided, such as providing just the catheter 12. The catheter 12 releasably connects with the imaging system.

The ICE catheter 12 includes an array 14 of elements 16 for imaging within a shaft or housing 20 having a tip 32, electrical conductors 22, steering wires 30, and a handle 21. Additional, different, or fewer components may be provided, such as radio opaque markers, ablation electrodes, lens, needle guide, or ports. In other embodiments, the catheter 12 is an ablation catheter or interventional catheter rather than an imaging catheter.

The shaft housing 20 is PEBAX°, nylon, polymer, or other flexible material. The shaft housing 20 is formed around the array 14 and other parts extending from the handle 21 and insertable into the patient. The shaft housing 20 is configured for insertion into a circulatory system of a patient. For example, the distal tip 32 of the catheter 12 includes a more flexible portion covered by the shaft housing 20 for moving through the circulatory system. Steering wires 30 connected to the shaft housing 20 or parts (e.g., anchors) within the housing 20 are configured to guide the shaft housing 20 within the circulatory system.

The array 14 is positioned within the catheter 12. The array 14 may fit within 10 French, 3.33 mm, 12.5 French, or another diameter catheter 12. The array 14 is at a distal end or tip 32 of the catheter 12, such as being within 20 mm of an end of the tip 32 or a beginning of a flexible tip portion. The array 14 may have any position within the catheter 12 that results in the array 14 being within the patient during use of the catheter 12 for imaging.

The transducer array 14 is used for ultrasound imaging. The images assist in diagnosis, catheter guidance, needle guidance, ablation guidance, placement, and/or needle puncture. The array 14 scans in a field of view 18 in a plane perpendicular to the emitting face. The patient within the field of view 18 may be imaged using the array 14.

Electrical conductors 22 connect the elements 16 of the array 14 to the beamformer 24. The conductors 22 are cables, coaxial cables, traces on flexible circuit material, wires, wire jumpers, combinations thereof, and/or other now known or later developed conductor.

The beamformer 24 includes a plurality of channels for generating transmit waveforms and/or receiving signals. Relative delays and/or apodization focus the transmit waveforms or received signals for forming beams and setting a focal location. The beamformer 24 connects with the conductors 22 for applying waveforms for imaging with the array 14 and receiving signals. For imaging, the beamformer 24 selects an aperture including one, some, or all of the elements 16 of the array 14. For scanning, the beamformer 24 electronically focuses along the azimuth direction. A plurality of scan lines using an aperture is scanned. During receive operations, the focus may vary as a function of depth (i.e., dynamic focusing).

The image processor 26 is a detector, filter, processor, application specific integrated circuit, field programmable gate array, digital signal processor, control processor, scan converter, three-dimensional image processor, graphics processing unit, analog circuit, digital circuit, or combinations thereof. The image processor 26 receives beamformed data and generates images on the display 28, which is a display screen.

The steering wires 30 of the catheter 12 are used to position the array 14 (and/or medical instrument) relative to the patient. The steering wires 30 are cables, tendons, or other structure for transferring push and pull force from the handle 21 to a portion of the catheter 12 within a patient, such as to the distal end or the tip 32. Any material may be used, such as plastic, fiberglass, or metal. Any number of steering wires 30 may be used, such as three or four wires. For example, three or four steering wires 30 offset from the center in an equal spacing about the center or longitudinal axis may be used to steer along two perpendicular planes. The steering wires 30 run through the elastic material of the catheter body or shaft housing 20 to the distal end and are arranged in a circular fashion around a central channel, which provides sufficient space for the ultrasound transducer cable or conductors 22 to be guided through. The relative force between the steering wires 30 causes the catheter 12 to bend. Any now known or later developed arrangement of steering wires 30 may be used.

In one embodiment, one knob 29 is provided for controlling the bend of the distal end in one plane. Two steering wires 30 connect with the knob 29, so rotation of the knob 29 causes a change in relative pressure or force on the steering wires 30. In another embodiment, two knobs 29 are provided. One knob 29 (e.g., AP knob) is for bending in one plane, such as an anterior-posterior (AP) plane, and another knob 29 (e.g., RL knob) is for bending in a perpendicular plane, such as a right-left (RL) plane.

The knob 29 rotates to steer. The knob 29 rotates about a longitudinal axis of the handle 21 and/or catheter 12. For example, the knob 29 is a cylinder or ring on the outer housing of the handle 21 for rotation about the axis in either direction to steer. In other examples, the knob 29 rotates around an axis perpendicular to the longitudinal axis of the handle 21. Alternatively, a slider or lever is provided as the knob 29 for steering.

The steering wires 30 control the bend at a distal end of the catheter 12. The bend may be at a portion of the catheter 12 adjacent to the distal end or tip 20, such as providing for the array 14 to be spaced from the handle 21 by the bend. For example, the steering wires 30 are anchored to the shaft housing 20, transducer array 14, or a rigid insert or anchor near the distal end to cause the bend. The elastic body or shaft housing 20 may be bent along its principal axes by applying tension to the attached steering wires 30. Using motors instead of user-based rotation of two knobs for two planes allows for only three steering wires 30 for forming the bend. Four steering wires 30 with motor-based control may be used, such as where the handle 21 is designed for manual operation.

The handle 21 includes a housing and user input in the form of one or more knobs 29 (see knob 40 of FIG. 3). The handle 21 is shaped and sized for handheld guidance or use of the catheter 12. For example, the handle 21 is cylindrical with grips to be used by one hand of a surgeon. The handle 21 has a single housing made of one or more parts. The housing connects with the shaft housing 20 of the catheter 12 and with a cable or cables for power and communications. In alternative embodiments, the housing is shaped for use with a robotic system rather than handheld guidance.

For robotic guidance, the catheter handle 21 is placed in an external actuation stage. The actuation stage forms a motor housing. Rather than handheld use, the actuation stage provides control for rotation, steering, and/or translation to be automated. The operator is then able to tele-operate the catheter 12 from a remote console, or a high-level motion planning algorithm may be used to generate spatial trajectories for the catheter tip 32.

A controller controls the robotic guidance. The controller is a processor, application specific integrated circuit, integrated circuit, digital signal processor, field programmable gate array, or other control device for controlling the motors of the robotic system. The controller is configured by design, hardware, and/or software to steer the catheter 12 using the user-based or other controls of the catheter 12, such as the handle 21 for rotation about a longitudinal axis of the catheter 12 and/or for translation along the longitudinal axis and one or more knobs 29 for steering (i.e., bending) the distal end.

FIG. 2 shows a system for guiding the catheter 12. The system is a robotic catheter system for rotating and/or steering the catheter 12. The system includes a base 34, a catheter handle housing 33 (carriage), an access point base 38, an access point guide 39, and an arm 36. Additional, different, or fewer components may be provided. For example, the arm 36, access point base 38, and access point guide 39 are not provided. As another example, the base 34 and the catheter handle housing 33 are combined into one housing or device.

Each of the parts has a housing. The housings are plastic, metal, resin, silicone, or other material.

The catheter handle housing 33 is configured to hold the handle 21 of the catheter 12. Any part of the handle 21 may be held, such as surrounding 50-90% of the outer surface of the handle 21. In one embodiment, the catheter handle housing 33 is a clam-shell shape with two halves. A hinge may be provided. Alternatively, the handle 21 is placed in a lower half, and then the upper half is placed over the lower half and latched to the lower half. Other arrangements, such as having two or more rings to hold the handle 21, may be used.

The cables with or without an end of the handle 21 may extend out of the catheter handle housing 33 when the handle 21 is positioned in the catheter handle housing 33. The shaft housing 20 with or without another end of the handle 21 may extend out of the catheter handle housing 33 when the handle 21 is positioned in the catheter handle housing 33. The knob 29 or knobs 29 are within or at least partly within the catheter handle housing 33.

Once positioned, one or more parts, such as rubberized or coated parts, form a pressure fit with the handle 21. For example, studs or one or more rings contact the handle 21 and are movable (e.g., rotatable) within the catheter handle housing 33. A separate set of studs or a ring contacts each knob 29 and are independently moveable (e.g., rotatable) within the catheter handle housing 33. As shown in FIG. 3, gears 41, 42, 43 connect with each of the rotatable parts. For the handle 21, the gear 43 is a circular gear surrounding and directly or indirectly contacting the handle 21. For the knobs 29, 40, knob gears 41, 42, respectively, are circular gears surrounding and directly or indirectly contacting the knobs 29, 40. The gears 41-43 are bevel gears, but flat or straight gears or gears with tracks on the side of a disc shape may be used. The gears 41-43 in the catheter handle housing 33 provide for driven rotation of the handle 21 and/or the knobs 29, 40.

The catheter handle housing 33 also includes gears 44, 45, and 51 for mating with and rotating the gears 41-43, respectively. The gears 44, 45, and 51 are bevel gears, but flat or straight gears or gears with tracks on the side of a disc shape may be used.

The gears 44, 45, and 51 and gears 41-43 form sets of gearing in the catheter handle housing 33 for transmitting force from the base 34 to the handle 21 and knobs 29, 40. This gearing is used to control the catheter robotically, such as the gearing of gears 44 and 41 and/or of gears 45 and 42 being for operating the anterior-posterior and/or left-right knobs 29, 40, respectively, for steering a distal end of the catheter 12. To steer, the knobs 29 and/or 40 are rotated relative to the handle 21, such as about the longitudinal axis of the handle 21, by the gearing.

Referring to FIGS. 2 and 3, the base 34 includes the housing around one or more motors 47, 48, and 53. The motors 47, 48, and 53 are within the base 34. The motors 47, 48, and 53 include shafts 46 and 52 for driving the gearing in the catheter handle housing 33, allowing for robotic manipulation of the catheter handle 21 and knobs 29, 40.

Figure 5:
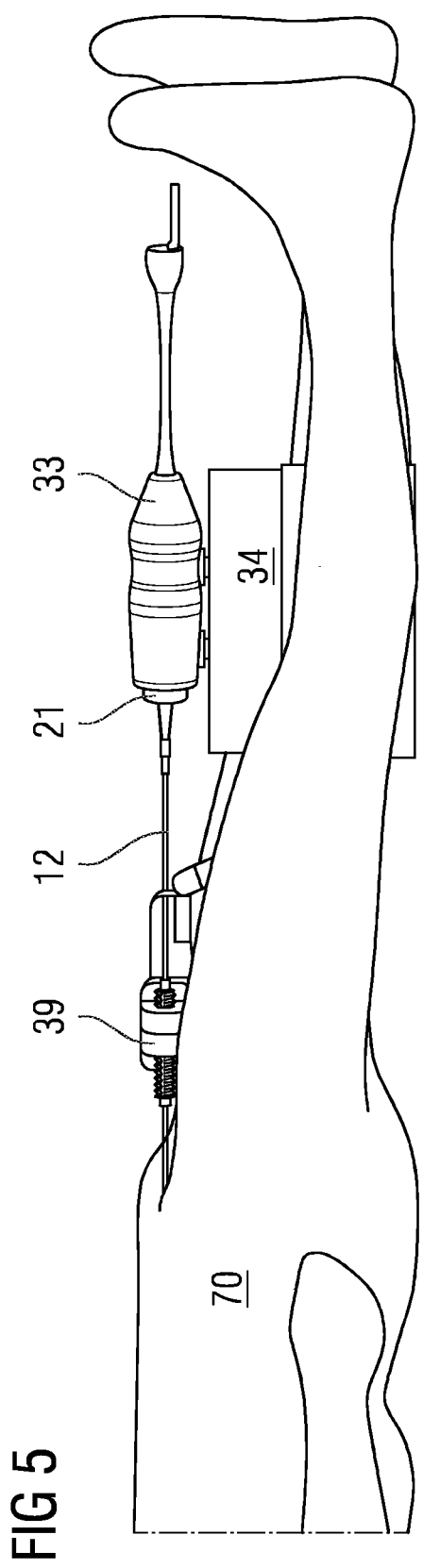
FIG. 5 illustrates positioning of a base for robotically guiding a cardiac catheter, such as an ICE catheter.

The housing of the base 34 has any size and shape. In one embodiment, the housing is prismoid, such as having six sides. The size and shape allow for placement on or by a table on which the patient lies. For example, the housing of the base 34 is less than 16 inches long, 12 inches high, and 6 inches wide. FIG. 5 shows an example with the base 34 sized and shaped to be placed on a table between the legs of the patient 70. This modular base 34 allows for placement at any desired position and orientation. The adjustable degrees of freedom and compactness of the base 34 allow for surgeries at different access points (e.g., femoral, radial, or jugular) and precise alignment of the catheter 12 with the sheath at the access point in the patient 70. The base 34 may be attached to the operating table or another table by magnets at the bottom (either a permanent magnet switch or electromagnets). Gravity, suction cups, latches, and/or other attachment devices may be used. Larger height, width, and/or length may be used.

Referring again to FIGS. 2 and 3, the base 34 connects with the catheter handle housing 33. The connection is through the shafts 46, 52, 58. A plastic or other transmission may be used to transfer force from the motors 47, 48, 53 to the gearing (i.e., to gears 44, 45, 51 and thus gears 41, 42, and 43, respectively). The rotations, including speed, direction, and amount, of the handle 21 and knobs 29, 40 are driven from the base 34.

In one embodiment, the base 34 connects to the gearing through a plastic interface of a sterile bag. The sterile bag includes one or more holes for the shafts 52 and 58. The catheter handle housing 33 and access point housing 39 are outside of the sterile bag while the base 34, arm 36, and access point base 38 are in the sterile bag, allowing re-use with less cleaning and avoiding discarding of expensive parts. Since all electronics in the base 34 are kept sterile in a procedure, the base 34 and electronics may be reused without cleaning. Since all parts not inside the bag are plastic or metal (i.e., the catheter handle housing 33 and gearing inside the catheter handle housing 33), these parts may be easily cleaned and reused.

The base 34 may include a rack holding the motors 47, 48, and 53 within the housing. The rack allows for shifting of position of the motors 47, 48, and 53 relative to the housing. One or more knobs 35 provide adjustment of the rack, resulting in shift of an interface plate 59, which interfaces with the catheter handle housing 33. The knobs 35 are rotatable but may be levers or sliders. In alternative embodiments, the relative position is set by hand with an electromagnetic brake to lock the position.

The interface plate 59 includes holes for the shafts 52 and 58 for mounting on, connection to, or fitting with the gearing in the catheter handle housing 33. The knobs 35 connect through gears, rack-and-pinion, belts, or other mechanical linkage to adjust a position of the motors 47, 48, and 53 relative to the base 34. For example, the height and fore-aft position of the base interface 59 may be manually adjusted using the two knobs 35 on the back or other location. The yaw of the base may be adjusted either by positioning the base differently on the table or by the pivot at the interface plate 59.

In one optional embodiment shown in FIGS. 2 and 3, an arm 36 extends from the base 34. The arm 36 includes any number and/or type of joints. For example, four links with three elbow joints are used. The arm 36 latches to or is formed as part of the base 34. Other connections to the base 34 may be used. Alternatively, the arm 36 mounts to the table or other device and is not connected directly to the base 34. The arm 36 is metal, rubber, fiberglass, plastic, and/or resin. The arm 36 may change position by manual adjustment. Alternatively, servo motors under electrical control adjust one or more joints. Any number of degrees of freedom may be provided.

The arm 36 supports the access point housing 39 with or without an access point base 38. The access point base 38 may include motors and gearing for moving an orientation (rotation) and/or position (translation) of the access point housing 39. The access point housing 39 holds the catheter 12, such as the shaft housing 20, at the access point or entry point into the patient. For example, the shaft housing 20 extends through an aperture formed by the access point housing 39, which is elongated to assist in preventing buckling.

The arm 36 provides an initial positioning and orientation of the access point housing 39 away from the handle 12 of the catheter and away from the base 34. The position and/or orientation of the access point housing 39 may be further adjusted in three dimensions using the poseable arm 36 in order to achieve the desired end-effector angle. The access point base 38 may manipulate the flexible catheter 12 itself, providing more direct control of the flexible catheter body or shaft housing 20 near its insertion point. This control or manipulation of the position and angle by the access point may reduce the chance of the catheter 12 buckling when pushed, pulled, or rotated in relation to the insertion sheath.

Referring to FIG. 3, the base 34 houses the motors 47, 48, and 53. The motors 47, 48, and 53 are servo motors, rotational motors, linear motors (e.g., linear magnetic motors), or other electric, pneumatic, or hydraulic motors for rotating the shafts 46, 58, and 52. Alternatively, gearing, clutch, and/or transmission is used to apply force from one motor to multiple shafts. In order to keep the electronics sterile, the controller and motors 47, 48, and 53 are spaced away from the catheter 12 by being positioned in the base 34.

One motor 53 rotates the shaft 52. Using the gearing of gears 51 and 43, the shaft rotation causes rotation of the gear 43, which rotates the entire catheter handle 21 within the catheter handle housing 33. The gear 51 is driven to rotate by the shaft 52 from the motor 53. By mating with the gear 43, the rotation of the gear 51 causes rotation of the gear 43 extending around the handle 21. The rotation of the handle 21 is about the longitudinal axis of the catheter handle 21 and the catheter 12.

To operate the knob 29 (e.g., RL knob), the motor 48 connects to the knob 29 through gearing. A motor shaft connects to and rotates a gear, which mates with a gear on the shaft 58. The shaft 58 rotates the gear 44, which mates with and rotates the gear 41. The gear 41 surrounds the knob 29 and causes the knob 29 to rotate. The knob 29 rotates relative to the handle 21. When the handle 21 is not rotating, any rotation of the knob 29 causes steering by the steering wires 30. When the handle 21 is rotating due to the motor 53, additional rotation applied to the knob 29 by the motor 48 causes steering by the steering wires 30.

Additional motors may be provided. In the embodiment of FIG. 3, the motor 47 is provided. To operate the knob 40 (e.g., AP knob), the motor 47 connects to the knob 40 through gearing. A motor shaft connects to and rotates a gear, which mates with a gear on the shaft 46. The shaft 46 rotates the gear 45, which mates with and rotates the gear 42. The gear 42 surrounds the knob 40 and causes the knob 40 to rotate. The knob 40 rotates relative to the handle 21. When the handle 21 is not rotating, any rotation of the knob 40 causes steering by the steering wires 30. When the handle 21 is rotating due to the motor 53, additional rotation applied to the knob 40 by the motor 47 causes steering by the steering wires 30.

In one embodiment, the shaft 46 is nested in the shaft 58. The shaft 58 is hollow. The shaft 46, with or without ball bearings, is positioned inside the shaft 58. In other embodiments, the shaft 58 is nested in the shaft 46. Alternatively, a transmission is used to control force from one shaft to the different gears 44, 45.

The motors 47, 48 control the catheter 12 bending through control of the amount and direction of rotation of the knobs 29, 40. To actuate the bending of the catheter 12 by tendons or steering wires 30 running along the catheter 12, the motors 47, 48 apply tendon pulling or pushing forces by knob rotation. To steer, the knobs 29, 40 apply relative push and/or pull forces on the steering wires 30, controlling the direction and magnitude of the bending. Any combination of relative forces may be used. The entire handle 21 may be rotated by any amount to rotate the catheter 12 and/or array 14. A shift in a bend plane may be provided by either rotating the handle 21 or by changing the forces on the steering wires 30. The motors 47, 48 may rotate AP and RL knobs 29, 40 to steer the distal end of the catheter 12 in two different planes.

Rotation of the catheter handle 21 would cause rotation of the knobs 29, 40 relative to their motors 47, 48 if the motors 47, 48 are not operated. That is, the knob rotations became coupled with the whole-body rotation due to the knobs 29, 40 being locked to the motors 47, 48 by the gearing. In one approach, the controller controls the motors 47, 48 to rotate the knobs 29, 40 at a same rate as the rotation of the handle 21 so that the relative rotation of the knobs 29, 40 to the handle 21 is zero. Due to the imprecise nature of a continuum manipulator such as a general catheter, it may be difficult to uncouple these degrees of freedom with the controller.

A mechanical decoupling is used. The motors 47, 48 are offset from the shafts 46, 58. The motor shafts are parallel but spaced from the shafts 46, 58. For example, the motor shaft of motor 47 connects to the shaft 46 through the gear 50. This offset allows for rotation of the motors 47, 48 about the shafts 46, 58. The rotation of the entire motors 47, 48 rotates the shafts 46, 58. The rate of rotation is set so that the mechanical rotation imparted to the shafts 46, 58 by rotation of the motors 47, 48 about the shafts 46, 58 matches the handle rotation. The knobs 29, 40 are mechanically rotated at a rate equal or similar to the rotation of the handle 21.

In the embodiment of FIG. 3, the motors 47, 48 are positioned in a cylindrical housing 49. The cylindrical housing 49 is metal, but plastic or other material may be used. In alternative embodiments, a ring surrounds the motors 47, 48 without the housing (e.g., gear 56 mechanically connects or links to the motors 47, 48 without the cylindrical housing 49).

The center axis of the cylindrical housing 49 aligns with or shares the same longitudinal axis of the centers of the shafts 46, 58. The motors 47, 48 are offset from this center axis. The cylindrical housing 49 rotates, causing rotation of the motors 47, 48 about this center axis of the cylindrical housing. The cylindrical housing 49 is used to mechanically decouple the rotation of the catheter body 12 and the rotation of the AP and RL knobs 29, 40. When the handle motor 53 causes a rotation of the handle 21, the cylindrical housing 49 containing the knob motors 47, 48 rotates as well. This rotation prevents relative rotations between the two knob motors 47, 48 and their respective knob gears 41, 42. Whether or not the handle motor 53 is rotating, the knob motors 47, 48 are free to affect their respective knobs 29, 40.

A transmission in the base 34 rotates the cylindrical housing 49. The transmission is gearing, such as being three gears 54, 55, and 56 with mating teeth. Other gearing, such as rack-and-pinion, pulley and belt, or screw gears may be used. These or other types of gears may be used for any of the gearing, such as the gearing for transmission of force from the motor 48 to the knob 29, from the motor 47 to the knob 40, and/or from the motor 53 to the handle 21.

The transmission for rotating the cylindrical housing 49 mechanically decouples actuation of the gear 43 from the gears 41, 42. When the handle motor 53 causes a rotation, the housing containing the knob motors 47, 48 rotates as well due to the transmission. This rotation prevents relative rotations between the two knob motors 47, 48 and their respective knob gears 41, 42. The rotation of the shaft 52 to rotate the handle 21 also rotates the gear 54. The gear 54 rotates the gear 55 about the shaft 57. The rotation of the gear 55 rotates the gear 56. The gear 56 is mounted to the cylindrical housing 49 and/or the knob motors 47, 48 so that the knob motors 47, 48 rotate with the gear 56. In alternative embodiments, the gear 54 mates with the gear 56 without the intervening gear 55, or additional intervening gears are provided.

The rotation by the motor 53 causes the handle 21 to rotate and also causes the motors 47, 48 to rotate about a center axis of the shafts 46, 58. The rotation of the catheter 12 about the longitudinal axis by the whole body motor 53 rotates the knob motors 47, 48, causing rotation of the knobs 29, 40 in a same direction and rate as the handle 21. Rotation of the gear 54 causes rotation of the gear 56, which causes rotation of the cylindrical housing 49 so that the knob gears 41, 42 rotate, allowing the knobs 29, 40 to maintain position relative to the handle 21 as the handle rotates.

This relative position is maintained while the motors 47, 48 are not active. If the one or both knob motors 47, 48 activate during handle rotation, the rotation of the motors 47, 48 decouples the knob rotation, so that the knob 29, 40 rotates relative to the rotating handle 21 to steer the catheter 12. The handle rotation rotates the steering plane. Within the steering plane, the knob rotation changes the bend of the catheter 12. Whether or not the handle motor 53 is rotating the shaft 52, the knob motors 47, 48 are free to affect their respective knobs 29, 40 due to the transmission from gears 54, 55, and 56 with the motors 47, 48 offset from the center of the shafts 46, 58. The knobs 29, 40 may be rotated by the motor 53 through the transmission to maintain position, rotated by the knob motors 47, 48 to change the bend, or rotated by both to account for handle rotation while also changing the bend.

Figure 4:
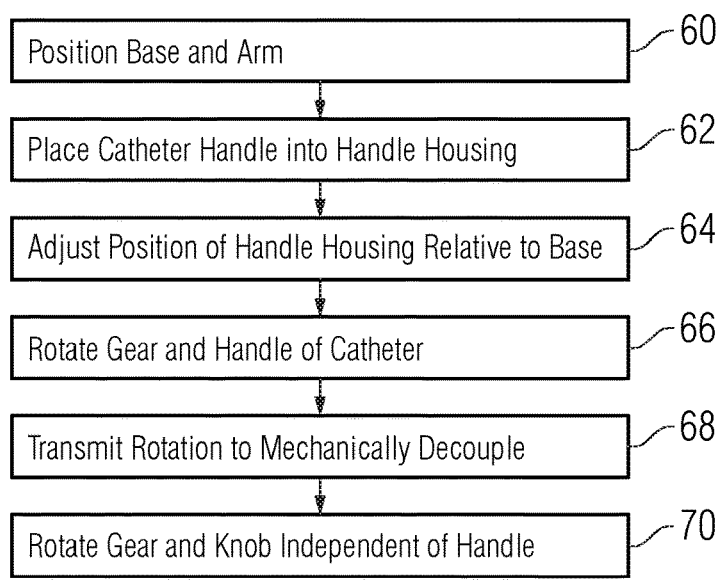
FIG. 4 is a flow chart diagram of one embodiment of a method for robotically operating a catheter.

FIG. 4 is a flow chart diagram of one embodiment of a method for robotically operating a catheter. The method includes positioning and orienting the catheter for insertion into the patient and robotic control of the position and orienting of the distal end of the catheter after insertion. A base design provides for ease of positioning for insertion and mechanical decoupling of handle rotation from knob rotation provides for ease of robotic control after insertion.

The method is implemented by the system and/or robotic system of FIGS. 2 and 3 or another system. The method uses the ICE catheter and imaging system of FIG. 1 or a different catheter. The method is described below using the catheter 12 of FIG. 1 and the robotic system of FIGS. 2 and 3.

Additional, different, or fewer acts may be provided. For example, acts 60-64 are not provided. As another example, act 68 is not provided. In yet another example, act 70 is not provided.

The acts are performed in the order shown or a different order. In the example of FIG. 4, acts 60-64 are performed to position for insertion, and acts 66-70 are performed for use as inserted. Act 70 may be performed prior to or during acts 66 and 68. Acts 66 and 68 are performed simultaneously. Act 62 may be performed prior to act 60 and/or after act 64.

In act 60, the base 34 and arm 36 are positioned. The base 34 is positioned relative to the patient. Depending on the point of access of the catheter 12 to the patient, the base 34 is positioned to align the catheter 12 with the patient and point of access. FIG. 5 shows an example where the base 34 is positioned for catheter 12 insertion into the femoral artery. The base 34 is positioned on a table or bed between the legs of the patient 70. The base 34 may be positioned relative to the patient at other locations, such as for access for the radial or jugular.

The base 34 rests on the table. Alternatively, the base 34 is attached to the table, such as by suction, magnetic, or mechanically (e.g., a latch or pin system).

The arm 36 is adjusted to place the access point housing 39 at the access point. A tip or exit location on the access point housing 39 is positioned against or by the already inserted sheath at the access point on the patient 70. The access point housing 39 is positioned by manual or robotic positioning of the arm 36. Upon desired positioning, the arm 36 is locked in place by one or more brakes, such as activated by the knob 37.

In act 62, the catheter 12 is placed in the robotic system. The handle 21 is placed in the handle housing 33. The handle housing 33 is closed around the handle 21 and latched in place to hold the handle 21.

This positioning occurs while the catheter handle housing 33 connects with the base 34. In one embodiment, the catheter handle housing 33 is separable from the base 34. The handle 21 is positioned in the catheter handle housing 33 while the catheter handle housing 33 is not attached to the base.

A sterile bag may be placed around the catheter 12. One or more holes are provided in the sterile bag, such as for the catheter 12 to extend into the patient and/or for the cable from the catheter handle 21 to connect to an imaging system. In one embodiment, the entire robotic system other than power and/or control cables and catheter exit point are placed in the sterile bag. In another embodiment, two holes are provided in the sterile bag for the shafts 52 and 58. The base 34 connects to the catheter handle housing 33 through a plastic interface with the two holes of the sterile bag. The catheter handle housing 33, the catheter 12, and the access point housing 39 are outside the sterile bag. The base 34, arm 36, and access point base 38 are in the sterile bag. Since all electronics are kept sterile by the bag, the electronics may be reused without cleaning or with a less intense cleaning. Since all parts not inside the bag are plastic or metal, these parts may be easily cleaned in-house and reused as many times as the catheter 12 is reused.

The shaft housing 20 of the catheter 12 may be inserted into the access point housing 39. The tip 32 of the catheter 12 is fed through an aperture of the access point housing 39. Alternatively, the access point housing 39 is a clam shell or has a removable side wall part to lay the shaft housing 20 in the access point housing 39. The insertion may feed the catheter 12 into the patient, such as through an already placed sheath. The handle 21 may be placed in the catheter handle housing 33 after or during insertion of the catheter shaft 20 through the access point housing 39 and/or into the patient 70.

In act 64, the position of the handle housing 33 relative to the base 34 may be adjusted. For example, the knobs 35 are activated or used to alter the position and/or orientation of the interface plate 59. The plate 59 and corresponding motors 47, 48, and 53 may be translated forwards or backwards and/or left or right. The plate 59 and corresponding motors 47, 48, and 53 may be rotated clockwise or counter clockwise. The plate 59 and corresponding motors 47, 48, and 53 may be angled upward or downward.

Once the catheter 12 is positioned in the patient and in the robotic system, the robotic system may be used to steer the distal tip through rotation of the catheter 12 and/or bending in one or more planes. The distal end and tip 32 are inserted into the patient 70. Any length of catheter 12 may be inserted. As the catheter 12 progresses into the patient 70, the catheter 70 may bend and/or twist with the vessel into which the catheter 12 is inserted. Steering may guide the catheter 12, such as applying force to steering wires to bend the catheter to progress in a given direction and/or rotating the handle 21.

The motors 47, 48, and 53 and motor drivers drive motions of the imaging device (e.g., array 14). While the catheter 12 is within the patient, the robotic system user may rotate the catheter 12. The catheter rotates about the longitudinal axis. For any bends caused by the vessel path, the catheter flexes to maintain the bend. For any bends caused by steering (i.e., force applied by the steering wires 30), the catheter 12 resists flexing to bend with the vessel. Where the bend is in a chamber, the rotation of the catheter 12 may not change the bend. The rotation of the catheter 12 would cause the plane of the bend to rotate.

The steering while the distal tip is within the patient 70 may be performed robotically. In acts 66-70, a controller controls one or more knob motors 47, 48 and the handle motor 53. Different knob motors 47, 48 connect to different knobs 29, 40 for controlling what would otherwise be manual steering with guide wires 30 using the knobs 29, 40. One or more bends are formed by active control of force provided by the knob motors 47, 48 in act 70. The orientation of the bending planes may be rotated by the handle motor 53 rotating the handle in act 66.

In act 66, the controller activates the handle rotation motor 53. This rotates the gear 51, which rotates the gear 43. The gear 43 is linked to the handle 21, such as through pressure contact or other mechanical linkage. The rotation of the gears 51 and 43 causes the handle 21 of the catheter 12 to rotate about a longitudinal axis of the handle 21.

In act 68, the rotation of the gear 43 and the handle 21 is transmitted to rotation of the knob gears 41, 42. The rotation of the gear 51, shaft 51, and the handle 21 is transmitted to rotation of the gears 44, 45, shafts 46, 58, and the knobs 29, 40. The rotation is transmitted through the gears 54, 55, and 56. In the embodiment of FIG. 3, the cylindrical housing 49 of the motors 47, 48 rotates due to the transmission. The off-center positioning of the motors 47, 48 causes rotation of the knobs 29, 40 through the gearing.

This transmission causes knob rotation not powered by the knob motors 47, 48, but instead powered by the handle motor 53. The transmitted rotation causes rotation of the knobs 29, 40 to match the rotation of the handle 21. By rotating the motors 47, 48 about the center of the shafts 46, 58, the knobs 29, 40 are rotated with the handle 21 despite being linked through gearing to the motors 47, 48. The motors 47, 48 may not be activated so act as a brake, yet the transmitted rotation of the motors 47, 48 moves the gears 41, 42 to move the knobs 29, 40 to move with the handle 21. Where the motors 47, 48 are activated during handle rotation, the extra rotation by the shafts of the motors 47, 48 causes extra rotation of the gears 41, 42, which alters the relative rotation of the knobs 29, 40 to the handle 21.

In act 70, one or more knobs 29, 40 are rotated to steer. The motor 47 rotates the motor shaft, which rotates the gear 50. Rotation of the gear 50 rotates the shaft 46, which rotates the gear 45. The rotation of the gear 45 rotates the gear 42, which rotates the knob 40, such as steering in the anterior-posterior plane.

The motor 48 rotates the motor shaft, which rotates gear mated with gearing on the shaft 58. Rotation of the shaft 58 rotates the gear 44. The rotation of the gear 44 rotates the knob 29, such as steering in left-right plane.

The knobs 29, 40 are rotated independently of each other and the rotation of the handle 21. When the handle 21 is not being rotated, the rotation of the gearing and knobs 29, 40 is not transmitted to the handle 21. When the handle 21 is being rotated, the knobs 29, 40 rotate with the handle 21 where the knobs 29, 40 are not activated to change steering. Where the steering or bending is to change, the motors 47, 48 cause the knobs 29, 40 to change position relative to the handle 21 even if the handle 21 is rotating.

During steering and/or after positioning, the catheter 12 is used. For an intervention catheter, drugs may be injected from the catheter 12 or a tool on the catheter 12 is used (e.g., scissors, needle, ablation electrode, scalpel, or another instrument).

For the imaging catheter of FIG. 1, the transducer is used for ultrasound scanning in a field of view. Ultrasound imaging is performed with the transducer. The user may view the surrounding tissue in different directions by rotating the catheter and/or other steering. Changes in bending may alter the field of view to image other anatomy or devices in the patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A robotic catheter system comprising:
   a first motor configured by a first gearing to rotate a catheter about a longitudinal axis;
   a second motor configured by a second gearing to rotate a first knob of a handle of the catheter; and
   third gearing connected between the first motor and the second motor so that the rotation of the catheter about the longitudinal axis by the first motor rotates the second motor to rotate the first knob.

2. The robotic catheter system of claim 1 wherein the second motor is a servo motor.

3. The robotic catheter system of claim 1 further comprising a catheter handle housing and a base housing, the first and second motors being in the base housing, and the first and second gearing being in the catheter handle housing.

4. The robotic catheter system of claim 3 wherein the base housing is less than 16 inches long, 12 inches high, and 6 inches wide.

5. The robotic catheter system of claim 3 further comprising an arm connected with the base, the arm being jointed and connected to an access point housing configured to hold the catheter away from the handle and at a point of entry into a patient.

6. The robotic catheter system of claim 3 wherein the base housing has a second knob configured to adjust a position of the first and second motors relative to the base.

7. The robotic catheter system of claim 1 wherein the first knob comprises an anterior-posterior or a left-right knob for steering a distal end of the catheter.

8. The robotic catheter system of claim 1 wherein the first knob is rotatable relative to the handle and about the longitudinal axis, and wherein the third gearing is configured so that the first knob maintains a position relative to the handle while the handle rotates with the rotation of the catheter while the second motor is not activated.

9. The robotic catheter system of claim 1 wherein the first gearing includes a first gear matable with a second gear, the second gear extending around the handle so that rotation of the first gear by the first motor causes rotation of the second gear about the longitudinal axis.

10. The robotic catheter system of claim 1 further comprising a cylindrical housing for the second motor, the third gearing including a gear with teeth around the cylindrical housing so that rotation of the first motor rotates the cylindrical housing and the second motor.

11. The robotic catheter system of claim 10 wherein the second motor is offset from a longitudinal center of the cylindrical housing wherein the second gearing includes a first shaft at the longitudinal center of the cylindrical housing so that the rotation of the cylindrical housing rotates the second motor about the longitudinal center.

12. The robotic catheter system of claim 11 further comprising a third motor within the cylindrical housing and fourth gearing connecting the third motor with a second knob of the handle, the fourth gearing including a second shaft at the longitudinal center of the cylindrical housing, the first shaft nested and rotatable independently of the second shaft.

13. A method for robotically operating a catheter, the method comprising:
   rotating a first gear linked to the catheter so that the rotating of the first gear causes a handle of the catheter to rotate about a longitudinal axis of the handle; and
   transmitting the rotation of the first gear to a second gear so that rotation of the second gear causes rotation of a third gear linked to a knob of the handle.

14. The method of claim 13 wherein rotating the first gear comprises rotating the first gear with a first motor, wherein a second motor is configured to rotate the third gear, and wherein transmitting comprises transmitting where the rotation of the third gear is from rotation of the second gear and not powered by the second motor.

15. The method of claim 14 wherein transmitting comprises rotating a motor housing of the second motor where the second motor is mounted off-center in the motor housing.

16. The method of claim 14 further comprising rotating the third gear by the second motor independently of the rotating of the first gear, the rotating the third gear not being transmitted to the first gear.

17. The method of claim 13 further comprising:
   positioning a base relative to a patient;
   placing the handle in a handle housing where the first gear is within the handle housing and connects with the base through a motor shaft; and
   adjusting a position of the handle housing relative to the base;
   wherein the rotating occurs after the adjusting.

18. A system for guiding a catheter, the system comprising:
   a handle housing configured to hold a handle of the catheter, the handle housing having a first gear to rotate the handle and a second gear to rotate a first knob on the handle;
   a base connectable with the handle housing so that the first and second gears are driven from the base; and
   an access point housing configured to hold a shaft of the catheter away from the handle, the access point housing configured to adjust an angle of the shaft relative to the handle.

19. The system of claim 18 further comprising a transmission in the base mechanically decoupling actuation of the first gear from the second gear, wherein the transmission comprises a third gear on a first shaft with the first gear, the third gear linked to a fourth gear on a housing of a first motor linked to a shaft with the second gear so that rotation of the first gear causes rotation of the third gear, which causes rotation of the housing so that the second gear rotates, allowing the first knob to maintain position relative to the handle.

20. The system of claim 19 further comprising a fifth gear connected with and between the third gear and the fourth gear.

21. The system of claim 18 further comprising an arm with one or more joints connecting the base to the access point housing, wherein the access point housing includes one or more motors for adjusting the angle.

\* \* \* \* \*